(12) United States Patent
Burzynski

(10) Patent No.: US 11,344,521 B2
(45) Date of Patent: *May 31, 2022

(54) METHODS FOR THE TREATMENT OF LEPTOMENINGEAL DISEASE

(71) Applicant: Burzynski Research Institute, Inc., Houston, TX (US)

(72) Inventor: Stanislaw R. Burzynski, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/079,207

(22) Filed: Oct. 23, 2020

(65) Prior Publication Data

US 2021/0038552 A1 Feb. 11, 2021

Related U.S. Application Data

(63) Continuation of application No. 16/622,230, filed as application No. PCT/US2018/036972 on Jun. 11, 2018.

(60) Provisional application No. 62/518,500, filed on Jun. 12, 2017.

(51) Int. Cl.
| | |
|---|---|
| *A61K 31/198* | (2006.01) |
| *A61K 31/216* | (2006.01) |
| *A61P 35/00* | (2006.01) |
| *A61K 9/00* | (2006.01) |

(52) U.S. Cl.
CPC .......... *A61K 31/198* (2013.01); *A61K 9/0019* (2013.01); *A61K 31/216* (2013.01); *A61P 35/00* (2018.01)

(58) Field of Classification Search
CPC .. A61K 31/198; A61K 31/216; A61K 9/0019; A61P 35/00
See application file for complete search history.

(56) References Cited

U.S. PATENT DOCUMENTS

| | | | |
|---|---|---|---|
| 6,258,849 B1 | 7/2001 | Burzynski | |
| 10,624,869 B2 | 4/2020 | Burzynski | |
| 2002/0103141 A1 | 8/2002 | McKearn et al. | |
| 2016/0158186 A1 | 6/2016 | Brown et al. | |
| 2018/0318421 A1 | 11/2018 | Burzynski | |

FOREIGN PATENT DOCUMENTS

WO  WO 2016/128146  8/2016

OTHER PUBLICATIONS

Burzynski et al., Drugs R&D 2004; 5 (6): 315-326 (cited as "Burzynski-1") (Year: 2004).*
Burzynski, Journal of cancer Therapy, 2015, 6, 1063-1074 (cited as "Burzynski-2") (Year: 2015).*
Moon et al., J Korean Neurosurg Soc. Feb. 2012; 51(2): 109-112 (Year: 2012).*
International Search Report and Written Opinion, dated Jul. 18, 2018, for the corresponding International Application No. PCT/US18/31456 in 10 pages.
Cecil Textbook of Medicine, 20th Edition, vol. 1, 1996, W.B. Saunders Company, edited by J. Claude Bennett, M.D. and Fred Plum, M.D.
Gura et al., Systems for identifying new drugs are often faulty, Science; Nov. 7, 1997; 278, 5340, ProQuest Central, p. 1041-1042.
Johnson et al., Relationships between drug activity in NCI preclinical in vitro and in vivo models and early clinical trials (British Journal of Cancer 2001), Cancer Research Campaign, 1424-1431.
Burzynski et al., Preliminary Findings on the Use of Targeted Therapy with Pazopanib and Other Agents in Combination with Sodium Phenylbutyrate in the Treatment of Gliobastoma Multiforme, Journal of Cancer Therapy, 2014, 5, 1423-1437.
Remington, The Science and Practice of Pharmacy, Nineteenth Edition—1995, vol. 2, Mack Publishing Company, Chapter 88, Intravenous Admixtures, 1549-1560.
Burzynski et al,, A Phase II Study of Antineoplastons A10 and AS2-1 in Adult Patients with Recurrent Glioblastoma Multiforme; Final Report (Protocol BT-21), Journal of Cancer Therapy, 2014, 5, 946-956.
Siegelin et al., Sorafenib exerts anti-glioma activity in vitro and in vivo, Neuroscience Letters 478, 2010, 165-170.
Verhaak et al., An integrated genomic analysis identifies clinically relevant subtypes of glioblastoma characterized by abnormalities in PDGFRA, IDH1, EGFR and NF1, National Institute of Health, NIG Public Access, Cancer Cell, Jan. 19, 2010, 17(1); 98.
International Search Report and Written Opinion, dated Sep. 7, 2018, for the corresponding International Application No. PCT/US2018/036972 in 8 pages.
Burzynski et al., "A Phase II Study of Antineoplastons A10 and AS2-1 in Children with Brain Tumors. Final Report (Protocol BT-10)", Feb. 16, 2017, Journal of Cancer Therapy, vol. 8.
Extended European Search Report dated Jan. 25, 2021, 6 pages, for the corresponding European Patent Application No. 18818116.8.
Burzynski et al., "Primary CNS Tumors and Leptomeningeal, Disseminated and/or Multicentric Disease in Children Treated in Phase II Studies with Antineoplastons A10 and AS2-1", Cancer and Clinical Oncology, vol. 5, No. 2, Oct. 10, 2016 (Oct. 10, 2016), p. 38, XP055765567, ISSN: 1927-4858, DOI, 10.5539/cco.v5n2p38.
Maria Estela Ceja, et al., "Dosing Considerations in Pediatric Oncology", U.S. Pharmacist, The Pharmacist's Resource for Clinical Excellence, published Jan. 23, 2013 in 9 pages; US Pharm. 2013; (38) (Oncology suppl): 8-11.

* cited by examiner

*Primary Examiner* — Jean P Cornet
(74) *Attorney, Agent, or Firm* — Polsinelli PC

(57) ABSTRACT

Methods for the treatment of leptomeningeal disease in a pediatric patient. The leptomeningeal disease may be leptomeningeal, disseminated, and/or multicentric disease (LDM) and may be associated with one or more primary CNS tumors or one or more low-grade gliomas (LGGs). The method includes administering to a patient a plurality of extraneous antineoplastons.

16 Claims, 3 Drawing Sheets

METHODS FOR THE TREATMENT OF LEPTOMENINGEAL DISEASE

CROSS REFERENCE TO RELATED APPLICATIONS

This application is a continuation of U.S. Ser. No. 16/622,230, filed Dec. 12, 2019, which is 35 U.S.C. 371 national stage filing of International Application No. PCT/US2018/036972, filed on Jun. 11, 2018, which claims priority to U.S. Provisional Application No. 62/518,500, filed on Jun. 12, 2017. The contents of the aforementioned applications are hereby incorporated by reference in their entireties.

FIELD OF TECHNOLOGY

The present disclosure is directed to methods of treating leptomeningeal disease and cancer. More specifically, the present disclosure is directed to methods for the treatment of leptomeningeal, disseminated, and/or multicentric disease (LDM) and primary central nervous system (CNS) tumors in children or adolescents.

BACKGROUND

Leptomeningeal disease occurs when brain tumor cells spread to the membranes (meninges) covering the brain and spinal cord resulting in leptomeningeal metastases (LM). Leptomeningeal, disseminated and/or multicentric disease (LDM) have been associated with a poor prognosis in childhood brain tumors when compared to solitary lesions. Dissemination refers to widespread involvement with the disease of the brain and spinal cord. "Multifocal" and "multicentric" gliomas, while difficult to differentiate, may at least in some instances be distinguished in that multifocal gliomas may be thought to disseminate along established CNS routes while multicentric gliomas may be widely separated in location and/or time. By this definition, multifocal glioma may consist of tumors separated by white matter tracts within the same hemisphere, whereas multicentric glioma may consist of widespread tumors, such as those occurring in opposite hemispheres or separated by the tentorium. Some have suggested that interstitial fluid along white matter tracts could be a potentially important mechanism for the dissemination of glioma cells and have postulated that glioma cells were inherently capable of migration along white matter tracts to distant areas of the brain. Multicentric disease and leptomeningeal metastases (LM) may also develop because of the unique propensity of glioma cells to invade normal brain tissues (or the spinal cord) and migrate long distances.

Low-grade gliomas (LGGs) are rare CNS neoplasms in pediatric patients. Childhood LGGs are a heterogeneous set of tumors, encompassing astrocytic, oligodendroglial, and mixed glial-neuronal histologies. Although their clinical behavior can vary, the majority of LGGs are indolent and do not undergo malignant transformation. Case reports have even described spontaneous regression of some tumors in contrast to adult LGGs that have a more aggressive phenotype. One reason for the differences between the two populations may be the different frequencies of histological subtypes. Pilocytic astrocytomas infrequently occur in adults but are the leading histology in children. Conversely, diffuse gemistocytic astrocytomas, which have been associated with an increased tendency toward malignant progression, are rarely found in children. LGGs are estimated to account for anywhere from 30% to 50% of CNS tumors in children.

The two most common LGG histologies in children are the pilocytic (grade 1) and diffuse fibrillary astrocytoma (grade 2). The former occurs mainly in children aged 5 to 19 years with a peak incidence in the 5- to 9-year-old age range (Central Brain Tumor Registry of the United States (2015) CBTRUS statistical report: Primary brain and central nervous system tumors diagnosed in the United States in 2008-2012. *Neuro-Oncology*, 17, iv1-iv62, Supplement 4, 2015). Diffuse fibrillary astrocytomas occur in an older population with only 10% occurring below the age of 20 years (CBTRUS, Supplement 4, 2015). Pilocytic astrocytomas can arise anywhere in the central nervous system; however, they predominate in the cerebellum, optic pathway, and dorsally exophytic brainstem. Conversely, diffuse fibrillary astrocytomas are more frequent in the supratentorial region, deep midline structures, and the cervicomedullary region. Other, less common, LGG histologies in children include pilomyxoid astrocytoma, pleomorphic xanthoastrocytoma, ganglioglioma, subependymal giant cell astrocytoma, and oligodendroglioma.

Leptomeningeal metastases (LM) has been reported in approximately 5% of LGG patients presenting with leptomeningeal dissemination at the time of diagnosis and 7%-10% presenting with LM at the time of disease progression (Perilongo, G., Garrè, M. L., & Giangaspero, F. (2003) Low grade glioma and leptomeningeal dissemination: a poorly understood phenomenon. *Child's Nervous System*, 19, 197-203.). The response criteria in LM differ between clinical studies, being based on a combination of radiologic (MRI), cytologic and clinical data.

It is estimated that as many as 30% of patients with primary CNS tumors have leptomeningeal, disseminated, and/or multicentric disease (LDM). These patients respond poorly to conventional therapy. Overall survival in patients with central nervous system (CNS) atypical teratoid rhabdoid tumor (AT/RT) is poor with a median survival around 17 months. There is no standard treatment for this rare tumor, but therapy for CNS AR/AT usually combines surgery, radiation therapy, and chemotherapy. Patients, including children, having leptomeningeal disease characterized by leptomeningeal metastases (LM) and/or leptomeningeal, disseminated and/or multicentric disease (LDM) are typically treated using temozolomide, carboplatin, irinotecan, and targeted therapy with bevacizumab and tipifarnib. However, in view of the unfavorable prognosis in children having leptomeningeal disease characterized by leptomeningeal metastases (LM) and/or leptomeningeal, disseminated and/or multicentric disease (LDM), when treated with currently available treatment modalities, new methods for the treatment for LM and LDM, as well as primary central nervous system (CNS) tumors are desirable.

BRIEF DESCRIPTION OF THE DRAWINGS

Examples of the present application are described with reference to the attached Figures, wherein.

Figure 1:
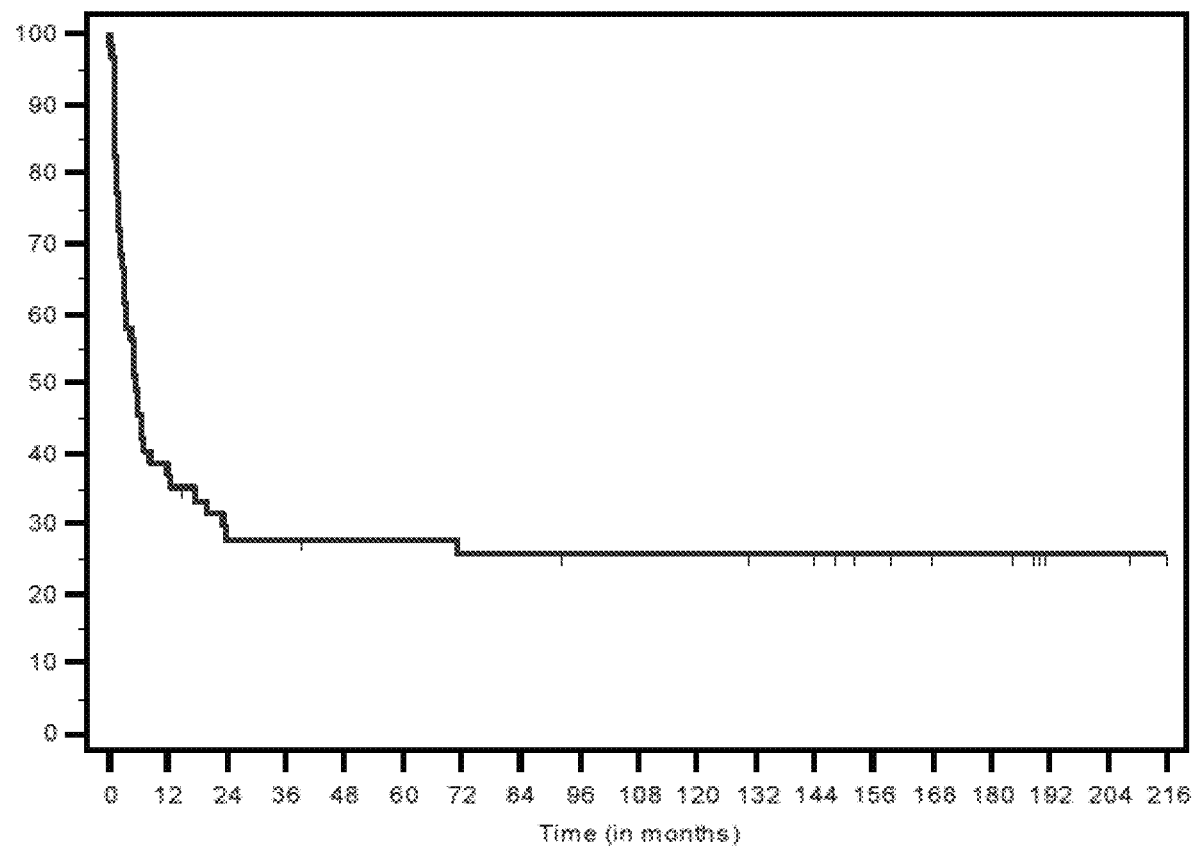
FIG. 1 is an illustration depicting a Kaplan-Meir survival curve for 57 children with CNS tumors and disseminated, leptomeningeal and/or multicentric disease, when treated according to an example of the present disclosure.

It should be understood that the various aspects are not limited to the depictions provided in the drawings.

DETAILED DESCRIPTION

Various examples of the disclosure are discussed in detail below. While specific implementations are discussed, it should be understood that this is done for illustration purposes only. A person skilled in the relevant art will recognize that other procedures and techniques can be used without parting from the spirit and scope of the present disclosure.

It should be understood at the outset that although illustrative implementations of one or more examples are illustrated below, the disclosed methods can be implemented using any number of techniques. The disclosure should in no way be limited to the illustrative implementations, drawings, and techniques disclosed herein, but can be modified within the scope of the appended claims along with their full scope of equivalents. In addition, numerous specific details are set forth in order to provide a thorough understanding of the examples described herein. However, it will be understood by those of ordinary skill in the art that the examples described herein can be practiced without these specific details. In other instances, methods, procedures and techniques have not been described in detail so as not to obscure the related relevant feature being described.

The following definitions are provided in order to aid those skilled in the art in understanding the present disclosure. As used herein, the term "objective response" refers to a response of a tumor to a therapeutic treatment. In at least some instances, the term "objective response" refers to a measured reduction in tumor size. The term "objective response" may include either a "complete response (CR)" or a "partial response (PR)," as defined herein. As used herein, the term "disseminated" refers to cerebrospinal fluid (CSF) dissemination which may result in multicentric disease and/or leptomeningeal metastases (LM). As used herein, the term "antineoplaston (ANP) therapy," refers to administration to a patient, by any administration route, of an "ANP therapeutic composition" comprising a therapeutically effective amount of Atengenal (A10), Astugenal (AS2-1), or any combination thereof.

The present disclosure provides methods for treating leptomeningeal disease in a pediatric patient. In at least some instances the leptomeningeal disease may be leptomeningeal, disseminated, and/or multicentric disease (LDM). In some instances, the leptomeningeal disease may be associated with one or more primary CNS tumors. In other cases, the leptomeningeal disease may be associated with one or more low-grade gliomas (LGGs). The method includes administering to a patient a plurality of extraneous antineoplastons. The plurality of extraneous antineoplastons may include phenylacetate (PN), phenylacetylglutaminate sodium (PG), phenylacetylisoglutaminate sodium (iso-PG), and any combination thereof.

In some instances, the plurality of extraneous antineoplastons includes about a 4:1 ratio of synthetic phenylacetylglutaminate sodium (PG) and synthetic phenylacetylisoglutaminate sodium (iso-PG). In such cases, administration may include intravenous administration of the plurality of extraneous antineoplastons to the patient at a dosage of from about 0.5 g/kg/day to about 20 g/kg/day. According to at least one aspect of the present disclosure, the plurality of extraneous antineoplastons may include phenylacetylglutaminate sodium (PG) and phenylacetylisoglutaminate sodium (iso-PG) and the method includes intravenous administration of the plurality of extraneous antineoplastons in the following amounts: from about 0.4 g/kg/day to about 16 g/kg/day phenylacetylglutaminate sodium (PG); and from about 0.1 g/kg/day to about 4 g/kg/day phenylacetylisoglutaminate sodium (iso-PG).

In other instances, the plurality of extraneous antineoplastons includes about a 4:1 ratio of phenylacetate (PN) and phenylacetylglutaminate (PG). In such cases, administration may include intravenous administration of the plurality of extraneous antineoplastons to the patient at a dosage of from about 0.08 g/kg/day to about 0.6 g/kg/day. According to at least one aspect of the present disclosure, the plurality of extraneous antineoplastons may include phenylacetate (PN) and phenylacetylglutaminate (PG), the method comprising intravenous administration of the plurality of extraneous antineoplastons in the following amounts: from about 0.064 g/kg/day to about 0.48 g/kg/day phenylacetate (PN); and from about 0.016 g/kg/day to about 0.12 g/kg/day phenylacetylglutaminate sodium (PG).

Antineoplastons (ANP) are peptides, amino acid derivatives and carboxylic acids which were initially isolated from the blood and urine of healthy subjects. Because ANP were found to be deficient in the blood of cancer patients, it was postulated that they may have anticancer activity. Antineoplastic activity of these compounds has been shown in a number of clinical and preclinical studies. ANP may be administered to a patient in the form of an ANP therapeutic composition that includes Atengenal (A10), Astugenal (AS2-1), or any combination thereof.

Atengenal (A10) comprises a 4:1 ratio of synthetic phenylacetylglutaminate sodium (PG) and phenylacetylisoglutaminate sodium (iso-PG). PG has a molecular weight of 286.26 and an empirical formula of $C_{13}H_{15}N_2NaO_4$. PG was first described by Thierfelder and Sherwin and is synthesized by the reaction of phenylacetyl chloride with L-glutamine in an aqueous solution containing sodium bicarbonate. PG is a hygroscopic white powder having a melting point of approximately 102° C. and is very soluble in water. The structural formula of PG is:

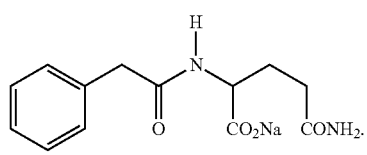

Iso-PG has a molecular weight of 286.26 and an empirical formula of $C_{13}H_{15}N_2NaO_4$. Iso-PG is synthesized by the reaction of phenylacetyl chloride with L-glutamine in an aqueous solution containing sodium bicarbonate to afford PG, which in turn is heated under vacuum at 160° C. to yield A10C (3-phenylacetylamino-2,6-piperidinedione). When A10C is treated with sodium hydroxide, it produces a mixture of PG and iso-PG in a 4:1 ratio. Iso-PG is a white powder having a melting point of approximately 175-176° C. and is soluble in water. The structural formula of iso-PG is:

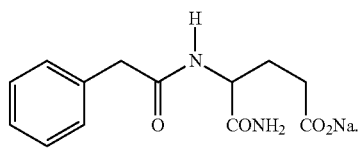

Astugenal (AS2-1) comprises phenylacetate (PN) and PG in a 4:1 ratio. PN is characterized by a molecular weight of 158.63 and an empirical formula of $C_8H_8NaO_2$. PN is synthesized by refluxing benzyl cyanide with dilute sulfuric acid or hydrochloric acid. In solid form, PN has a melting point of approximately 76.5° C. The structural formula of PN is:

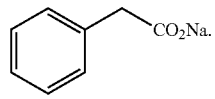

In at least some instances, ANP therapeutic compositions may be administered to a patient intravenously using, for instance, a dual-channel infusion pump and central venous catheter. In some cases, intravenous administration of ANP therapeutic compositions may occur once every four hours at the infusion rate of from about 50 mL/hr to about 250 mL/hr depending on patient's age and condition/tolerance, in an outpatient setting. AS2-1 or A10 can be administered separately or in combination.

The plurality of extraneous antineoplastons may be administered intravenously to a patient. In some instances, the plurality of extraneous antineoplastons may include phenylacetylglutaminate sodium (PG) and phenylacetylisoglutaminate sodium (iso-PG). For example, the plurality of extraneous antineoplastons may be the Atengenal (A10) composition describe above. In such instances, the plurality of extraneous antineoplastons may include about a 4:1 ratio of PG and iso-PG. In at least some instances, the plurality of extraneous antineoplastons comprising PG and iso-PG may be administered intravenously to a patient at a dosage of from about 0.5 g/kg/day to about 25 g/kg/day. In other instances, the plurality of extraneous antineoplastons comprising PG and iso-PG may be administered intravenously to a patient at a dosage of from about 2 g/kg/day to about 8 g/kg/day. In at least some instances the optimal dose of extraneous antineoplastons comprising PG and iso-PG may be about 4 g/kg/day.

The plurality of extraneous antineoplastons may be administered intravenously to a patient at a dosage of from about 0.4 g/kg/day to about 20 g/kg/day phenylacetylglutaminate sodium (PG) and from about 0.1 g/kg/day to about 5 g/kg/day phenylacetylisoglutaminate sodium (iso-PG). In other instances, the plurality of extraneous antineoplastons may be administered intravenously to a patient at a dosage of from about 1.6 g/kg/day to about 6.4 g/kg/day phenylacetylglutaminate sodium (PG) and from about 0.4 g/kg/day to about 1.6 g/kg/day phenylacetylisoglutaminate sodium (iso-PG). In at least some instances, the optimal dose of phenylacetylglutaminate sodium (PG) may be 3.2 g/kg/day and the optimal dose of phenylacetylisoglutaminate sodium (iso-PG) may be 0.8 g/kg/day.

In some instances, the plurality of extraneous antineoplastons may include phenylacetate (PN) and phenylacetylglutaminate (PG). For example, the plurality of extraneous antineoplastons may be the Astugenal (AS2-1) composition described above. In such instances, the plurality of extraneous antineoplastons may include about a 4:1 ratio of PN and PG. In at least some instances, the plurality of extraneous antineoplastons comprising PN and PG may be administered intravenously to a patient at a dosage of from about 0.04 g/kg/day to about 0.6 g/kg/day. In other instances, the plurality of extraneous antineoplastons comprising PN and PG may be administered intravenously to a patient at a dosage of from about 0.2 g/kg/day to about 0.4 g/kg/day. In at least some instances the optimal dose of extraneous antineoplastons comprising PN and PG may be about 0.4 g/kg/day.

The plurality of extraneous antineoplastons may be administered intravenously to a patient at a dosage of from about 0.064 g/kg/day to about 0.48 g/kg/day phenylacetate (PN) and from about 0.016 g/kg/day to about 0.12 g/kg/day phenylacetylglutaminate sodium (PG). In other instances, the plurality of extraneous antineoplastons may be administered intravenously to a patient at a dosage of from about 0.16 g/kg/day to about 0.48 g/kg/day phenylacetate (PN) and from about 0.04 g/kg/day to about 0.12 g/kg/day phenylacetylglutaminate sodium (PG). In at least some instances, the optimal dose of phenylacetate (PN) may be 0.32 g/kg/day and the optimal dose of phenylacetylglutaminate sodium (PG) may be 0.08 g/kg/day.

In at least some instances, the plurality of extraneous antineoplastons may include phenylacetylglutaminate sodium (PG), phenylacetylisoglutaminate sodium (iso-PG), phenylacetate (PN), and any combination thereof.

In at least some instances, the ANP therapy may begin on day 1 with escalating dosages administered on days 2-4. ANP therapy may then continue daily for the duration of the treatment regimen. The treatment regimen may continue, for example, for 8 weeks. An MRI scan may then be used to determine if an objective response has occurred. The treatment regimen may then be repeated as needed, with or without the staggered onset of concurrent administration.

Fifty-seven pediatric patients (age<18 years) with primary central nervous system (CNS) tumors and LDM were treated with ANP therapy in phase II studies at the Burzynski Clinic (BC) in Houston. The median age was 7.1 years old. These phase II studies had been developed at the Burzynski Research Institute, Inc. (BRI), reviewed by the FDA, and approved by the Institutional Review Board (BRI-IRB). Of the 57 children treated in this program, 34 of these children (60%) were given permission by the FDA to be treated as compassionate exception (CE) patients since they did not meet all of the stated inclusion/exclusion criteria. CE patients received the same treatment as study patients.

All patients with primary glioblastoma multiforme (GBM) were excluded. The median Karnofsky or Lansky performance score at baseline was 60 (range 20-100). Signed informed consent documents were obtained from the children's legal guardians before enrollment. Distribution of the primary CNS tumors by histology and location are presented in Table 1. This report examines the objective response (OR) and overall survival (OS) rates and treatment tolerance in this group of children and presents two illustrative clinical cases of multicentric glioma.

TABLE 1

| Histology and Location | No of Patients |
| --- | --- |
| Diffuse intrinsic pontine glioma (DIPG) | 5 |
| Brainstem glioma (BSG) | 5 |
| Anaplastic astrocytoma (AA) | 3 |
| Anaplastic ependymoma | 4 |
| Astrocytoma, pilocytic-spine | 1 |
| Astrocytoma/astrocytoma pilocytic | 6 |
| Astrocytoma-brain-spine-disseminated | 1 |
| Atypical teratoid/rhabdoid tumor (AT/RT) | 3 |
| Choroid plexus carcinoma | 2 |
| Ependymoma | 2 |
| Ganglioglioma | 1 |
| Meningioma | 1 |
| Oligodendroglioma-spine | 1 |
| Primitive neuroectodermal tumor (PNET) | 18 |
| Optic pathway glioma (OPG) | 4 |

The 57 children included in the study had participated in prospective single-arm, two-stage, interventional phase II trials of ANP therapy. The sample size for each clinical trial was calculated based upon the method of Chang and colleagues (Chang, S., Kuhn, J. G., Robins, H. I., Schold, S. C., Spence, A. M., . . . Prados, M. D., (1999) Phase II study of phenylacetate in patients with recurrent malignant glioma: A North American Brain Tumor Consortium report. *Journal of Clinical Oncology* 17, 984-990.). The primary end-point of each clinical trial was the objective response (OR) rate. Every child had magnetic resonance imaging (MRI) of the brain and/or spinal column, with gadolinium enhancement, within two weeks of starting ANP therapy and every eight weeks thereafter. For all measureable ($\geq 5$ mm) enhancing lesions on the baseline T1-weighted MRI images, the product of the greatest perpendicular diameters was calculated and the sum of these products determined. To identify objective response (OR) to ANP therapy, this baseline sum was compared to the sum of these products as determined from the T1-weighted images, or follow-up MRIs.

No study or CE children who participated in phase II studies at BC were excluded from the initial analysis and all children who met the criteria of LDM were included in the study. Inclusion and exclusion criteria were unique to each phase II study and included patients with newly diagnosed and persistent/recurrent disease. Those with persistent/recurrent disease had undergone surgery, radiotherapy, and/or chemotherapy. Patients$\geq 18$ years of age or with GBM were excluded. The high prevalence of multicentric disease in GBM necessitates separate analysis.

ANP therapy was delivered via a dual chamber infusion pump and a subclavian venous catheter which delivered a ANP composition having A10 and AS2-1. The pump was programmed to infuse doses of A10 and AS2-1 given every four hours (e.g., six times daily). The average doses of the ANP therapy was 8.77 g/kg/d for A10 and 0.35 g/kg/d for AS2-1. No other anti-cancer treatment was permitted. The response to ANP therapy was monitored by MRIs every 8 weeks. Each child was treated for three or more weeks and instruction in the maintenance of ANP therapy was provided to the child (as possible) and to the legal guardian. At the treating physician's discretion, and after completion of training, in the home administration of ANP therapy, each child was sent home under the supervision of a local sub-investigator. Reasons for stopping ANP therapy included patient (or legal guardian) request, worsening of a child's clinical condition, an intolerable adverse event (AE), and progressive disease (PD).

Medications that were considered necessary for the child's welfare and that did not interfere with the evaluation of tumor response to ANP therapy were given at the discretion of the child's treating physicians. Corticosteroid dosages were based on symptoms and signs of increased intracranial pressure and were adjusted, as necessary, to maintain neurologic stability.

Objective responses to ANP therapy included a complete response (CR) and a partial response (PR). As used herein, a "complete response (CR)," refers to the disappearance of all enhancing disease on T1-weighted MRI images that was sustained for at least four weeks. The patient was off corticosteroids during this four week period or on a physiologic replacement dose to maintain neurologic stability. As used herein, a "partial response (PR)" refers to a $\geq 50\%$ decrease in the sum of the products of the greatest perpendicular diameters of all measureable enhancing lesions on T1-weighted MRI images, as compared to baseline, that was sustained for a minimum of four weeks and the patient was on stable or decreasing doses of corticosteroids. Cerebrospinal fluid (CSF) analysis was performed during this four week period when possible, but was not used as a critical criterion in the evaluation of an objective response (OR).

Overall survival (OS) was determined from the first day that any ANP therapy was received until death from any cause. Surviving children were censored at the date of their last follow-up and the distributions of survival were estimated by Kaplan-Meier analysis using MedCalc Statistical Software, version 14.12.0, (MedCalc Software bvba, Ostend, Belgium).

All patients included in this review were treated in a similar fashion. Therefore, efficacy and toxicity are presented in summary fashion. Excluding patients with a diagnosis of GBM, 673 patients were treated in phase II studies of ANP therapy. Of these, 312 (46.4%) were children (<18 years). In these children, 57 cases (18.3%) of disseminated, leptomeningeal, and/or multicentric disease were identified. Patients evaluable for efficacy (N=40) received 12 or more weeks of ANP or developed progressive disease (PD) before 12 weeks. Ten of these 57 children achieved an objective response (OR) (17.5%), 4 achieved a complete response (CR) (7%) and 6 achieved a partial response (PR) (10.5%). Table 2 provides a summary regarding these ten cases, including the best response in ten children with CNS tumors and disseminated, leptomeningeal and/or multicentric disease (LDM) who participated in Phase II clinical trials of ANP therapy and achieved an objective response.

TABLE 2

| Case | Age (Years) | Patient Type | Diagnosis | Disease Type | Best Response |
| --- | --- | --- | --- | --- | --- |
| 1 | <1 | S | Visual pathway astrocytoma (pilocytic astrocytoma) | M | PR |
| 2 | 4 | CE | Atypical teratoid/rhabdoid tumor | L, M | CR |
| 3 | 4 | S | Visual pathway astrocytoma, low grade | M | PR |

TABLE 2-continued

| Case | Age (Years) | Patient Type | Diagnosis | Disease Type | Best Response |
|---|---|---|---|---|---|
| 4 | 6 | S | Visual pathway astrocytoma (pilocytic astrocytoma of the optic chiasm, optic tract, and hypothalamus) | M | CR |
| 5 | 8 | S | Ganglioglioma | M | PR |
| 6 | 8 | CE | Oligodendroglioma of the spinal cord | D, M | PR |
| 7 | 9 | S | Astrocytoma of the thalamus and brainstem, grade 2 | M | PR |
| 8 | 9 | S | Pilocytic astrocytoma, grade 1 | L, D, M | PR |
| 9 | 15 | S | Low grade astrocytoma | M | CR |
| 10 | 16 | CE | Pilocytic astrocytoma of the pineal region and spinal cord | L, D, M | CR |

Note:
CE = compassionate exception patient; CR = complete response; D = disseminated disease; L = leptomeningeal disease; M = multicentric disease; PR = partial response; S = study patient.

Stable disease (SD) was maintained in 7 patients (12.3%) and progressive disease (PD) developed in 23 patients (40.4%). Overall survival (OS) was determined for the group of 57 children based on the 15 surviving children (26.3%) censored at the date of their last follow-up. Overall survival data are illustrated in FIG. 1, which provides the Kaplan-Meier Survival curve. Two- and five-year overall survival were both 28% while 10- and 15-year overall survival were both 26%. The majority of the responding children were diagnosed with low-grade gliomas (LGGs).

Table 3 describes the number of deaths and the number of children censored at the date of their last follow-up, corresponding to the date of the Kaplan-Meier survival analysis. Based on these findings, in has been unexpectedly found that ANP therapy is particularly effective in the treatment of leptomeningeal disease including leptomeningeal, disseminated, and/or multicentric disease (LDM). Ten of the 57 children (17.5%) exhibited an objective response to ANP therapy. Four of 21 children with leptomeningeal disease achieved an OR (19%), with two children (9.5%) achieving a partial response (PR), and two children (9.5%) achieving a complete response (CR). While the differentiation of multicentric and multifocal disease is problematic and awaits further definition, leptomeningeal disease is well defined.

TABLE 3

| Number of Deceased (%) | Number Censored at Date of Last Follow-Up (%) | Number of Children in Total (%) |
|---|---|---|
| 42 (73.7%) | 15 (26.3%) | 15 (26.3%) |

All adverse events (AEs) were classified and graded according to CTCAEv.3.0. Grade 3 and 4 toxicities included hypokalemia (14.0%); fatigue, anemia, hypernatremia and leukopenia (3.5% each); diarrhea, hypertension, joint pain, thrombocytopenia, and somnolence (1.8% each).

EXAMPLES

Figure 2A:
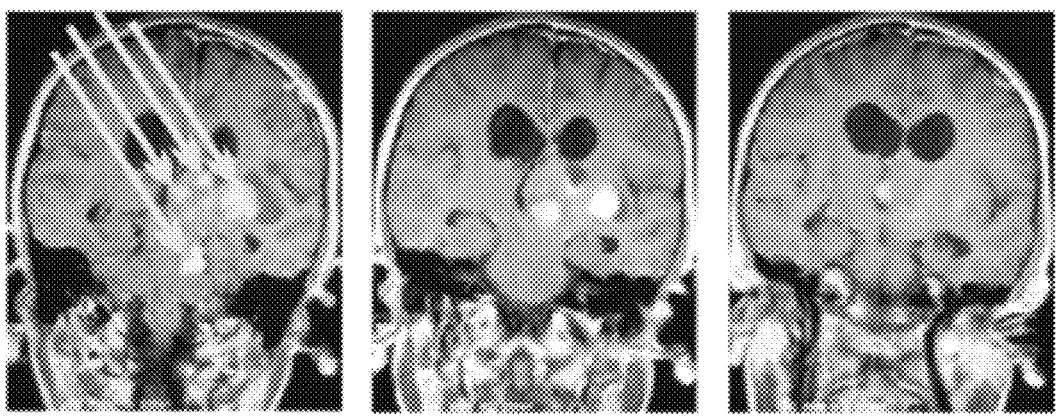
FIG. 2A is an illustration depicting a baseline MRI showing multicentric astrocytoma, grade 2, in a 10-year-old female, according to an example of the present disclosure.

Example 1: A healthy 10-year-old white female developed a tremor of her right hand and leg. MRI evaluation at the university hospital confirmed the presence of a tumor located in the left side of the thalamus and extending to the upper brainstem. The child underwent a craniotomy with subtotal tumor resection a few months after diagnosis. Histologic examination of the resected tumor specimen showed a grade 2 astrocytoma. She did not have adjuvant radiation therapy or chemotherapy. A baseline MRI of the brain approximately two weeks after resection showed progression of her disease, as shown in FIG. 2A.

The patient was evaluated at the Burzynski Clinic and enrolled in a phase II study of ANP therapy in children with a low-grade astrocytoma (protocol BT-13). The patient was intravenously administered an ANP therapeutic composition comprising A10 and AS2-1 six times daily. Over the course of treatment, the dosage of A10 was gradually increased to 7 g/kg/d. After 250 days at that dosage, the dosage of A10 was gradually increased to 12.6 g/kg/d, which was maintained for a period of 40 days and then reduced to 7.5 g/kg/d. Over the entire course of ANP therapy, the median dose of A10 was 6.8 g/kg/d while the median dose of AS2-1 was 0.34 g/kg/d. ANP therapy was permanently discontinued approximately 31 months following the beginning of ANP therapy, but the child continued oral formulations of A10 and AS2-1 for an additional 5 months.

Figure 2B:
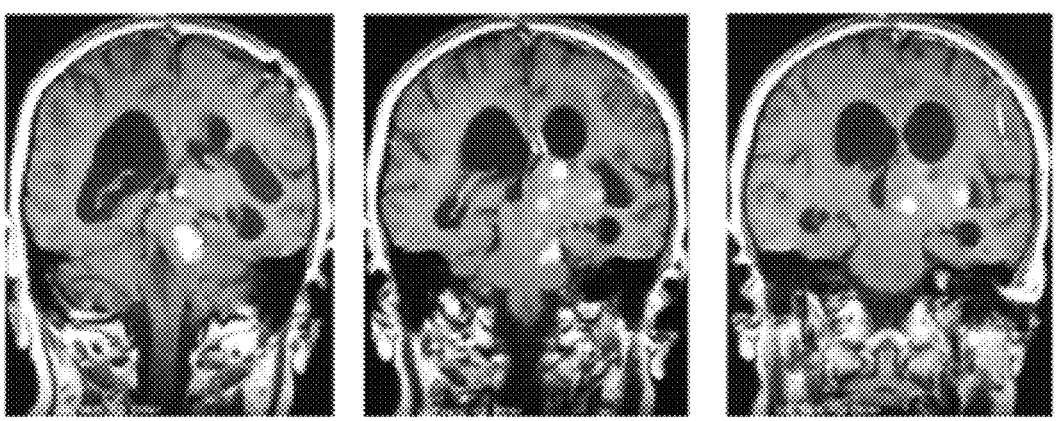
FIG. 2B is an illustration depicting a first follow-up MRI, acquired after 4 months of ANP therapy and showing a partial response, according to an example of the present disclosure.
Figure 2C:
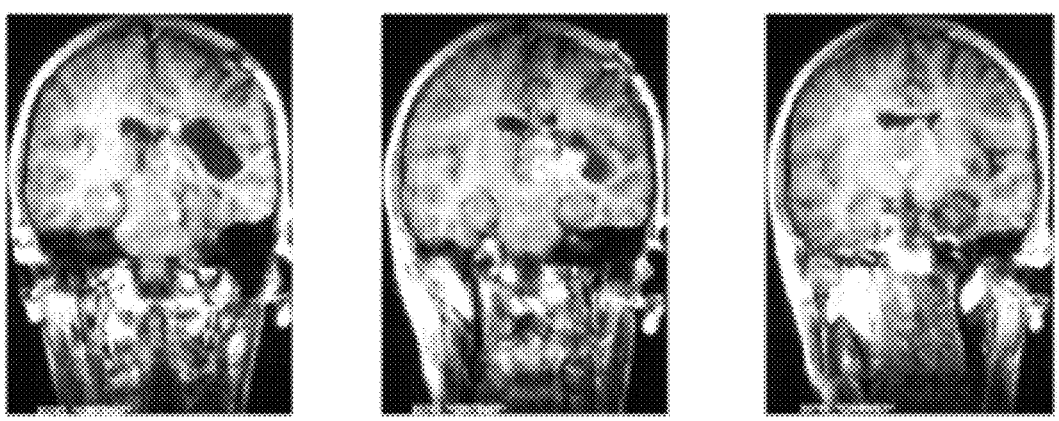
FIG. 2C is an illustration depicting a third follow-up MRI, acquired after 33 months of ANP therapy, showing persistence of the partial response, according to an example of the present disclosure.

Evaluation of the baseline MRI by an independent outside radiologist found the child to have seven measureable, enhancing brain and brainstem lesions. The sum of the products of the greatest perpendicular diameters of these seven lesions (SUM) was 10.88 cm$^2$. After 4 months of ANP therapy, a first follow-up MRI was acquired, as shown in FIG. 2B. A second follow-up MRI was acquired after 5 months of ANP therapy, which revealed the sum of the products to be 5.22 cm$^2$, a decrease of 52% from the baseline MRI. A third follow-up MRI was acquired after 33 months of treatment, as shown in FIG. 2C.

The child had achieved a partial response (PR) that persisted more than 28 months following the first administration of ANP therapy, with the greatest percent reduction in the sum of the products being 74.7%. During the time period of the partial response (PR), the child's corticosteroid dosages fell from 4 mg/d to 2 mg/d 28 months later. However, from one year after first ANP therapy administration to 21 months after first administration, the child's corticosteroid dosages were≤1 mg/d and from 21 months after first administration until 32 months after first administration, the patient did not receive corticosteroids.

Over the course of her ANP therapy, the child experienced eight Grade 1 and 2 adverse events (AEs) that were possibly related to ANP therapy: 1) fatigue, 2) vomiting, 3) nausea, 4) somnolence/depressed level of consciousness, 5) blurred vision, 6) allergic reaction, 7) rigors/chills, and 8) hot flashes/flushes. All of these adverse events (AEs) resolved with ANP therapy dose reduction or temporary discontinuation of ANP therapy.

The last documented contact with the patient was approximately 16 years after the first administration of ANP therapy.

At that time, the patient, age 26, had persistent right arm tremors but had been maintaining a good quality of life with a Karnofsky performance status of 90. There had been no long-term disability or chronic toxicity related to ANP therapy. The patient had not received any additional anti-cancer therapy since ANP therapy was discontinued and had not been taking any prescription medications.

Example 2: A healthy seven-year-old white female developed difficulty reading. Ophthalmologic examination showed blurring of the right optic disc consistent with optic nerve atrophy. MRI evaluation at the university hospital confirmed the presence of a tumor involving the optic chiasm, hypothalamus, and left hemisphere. The child underwent stereotactic biopsy on a couple of months following the onset of symptoms. Histologic examination of the biopsy specimen showed a pilocytic astrocytoma. She was not a candidate for tumor resection or stereotactic radiotherapy.

The patient was evaluated at the Burzynski Clinic and enrolled in a phase II study of ANP therapy in children with visual pathway glioma (protocol BT-23), and began ANP therapy one month following resection. The patient was intravenously administered an ANP therapeutic composition comprising A10 and AS2-1 six times daily. The dosage of A10 was gradually increased to a maximum of 18.81 g/kg/d. Over the entire course of ANP therapy, the median dose of A10 was 10.85 g/kg/d while the median dose of AS2-1 was 0.45 g/kg/d. ANP therapy was permanently discontinued 9 months after the first ANP administration. However, oral formulations of A10 and AS2-1 were administered to the child for an additional 3 years and 8 months.

Figure 3A:
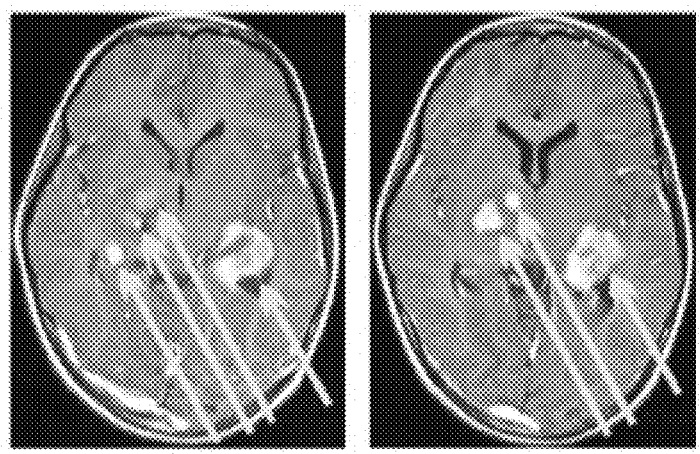
FIG. 3A is an illustration depicting a baseline MRI, showing a multicentric pilocytic astrocytoma in a 7-year-old female, according to an example of the present disclosure.
Figure 3B:
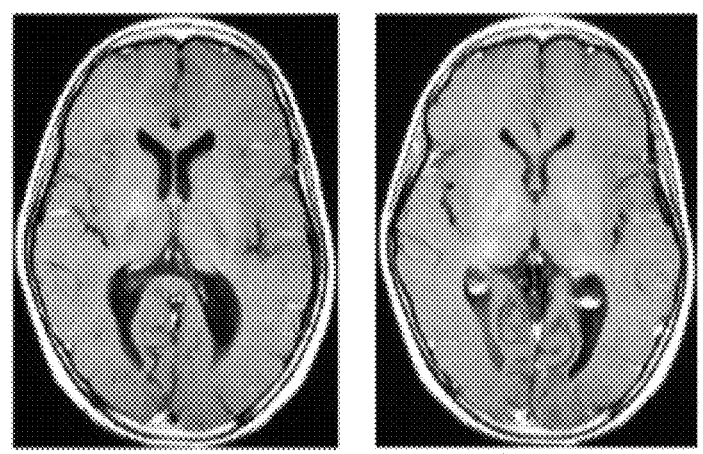
FIG. 3B is an illustration depicting a second follow-up MRI, acquired after 43 months of ANP therapy and showing a complete response, according to an example of the present disclosure.
Figure 3C:
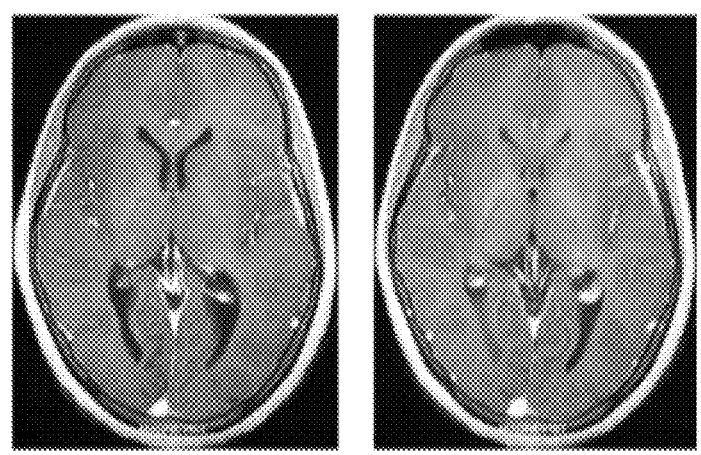
FIG. 3C is an illustration depicting a third follow-up MRI, after 106 months of ANP therapy, showing persistence of the complete response, according to an example of the present disclosure.

A baseline MRI acquired prior to the first administration of ANP therapy, shown in FIG. 3A, was evaluated by an independent outside radiologist whom found the child to have three measureable, enhancing brain lesions. The sum of the products of the greatest perpendicular diameters of these three lesions (SUM) was 16.49 cm$^2$. A subsequent first follow-up MRI, acquired after 5 months of ANP therapy, revealed the sum to be 4.48 cm$^2$, a decrease of 72.8% from baseline, while evaluation of a second follow-up MRI, acquired 38 months later, indicated that a complete response (CR) had been achieved, as shown in FIG. 3B. FIG. 3C also depicts a third follow-up MRI, acquired 106 months following the first administration of ANP therapy, indicating the persistence of the completer response (CR). The follow-up contrast-enhanced MRIs indicate the disappearance of multicentric nodules compared to the baseline MRI confirming complete response to ANP.

Further, a PET scan acquired 5 months after administration of the first ANP therapy showed no tumor activity. Repeat PET scans acquired 39 months, 53 months (just after permanent discontinuation of the oral formulations of A10 and AS2-1), and 58 months following the first administration of ANP therapy, also showed no tumor activity, providing supporting evidence of the complete response observed on the MRI scans. From four months to five months following first administration of ANP therapy, the child was off corticosteroids, but intermittently received small doses of corticosteroids after that period. From seven months to eleven months following the first administration of ANP therapy, when corticosteroids were permanently discontinued, the patient received≤1 mg of oral corticosteroids per day.

Over the course of her ANP therapy, the child experienced 6 Grade 1 and 2 adverse events (AEs) that were possibly related to ANP therapy. All of these adverse events (AEs) resolved with ANP therapy dose reduction or temporary discontinuation of ANP therapy.

The last documented follow-up with the patient's father was 15 years 8 months after the first administration of ANP therapy. At that time, the patient, age 22, the patient was maintaining an excellent quality of life with no evidence of tumor recurrence. There has been no long-term disability related to ANP therapy. The patient has not received any additional anti-tumor therapy since ANP therapy was discontinued.

Numerous examples are provided herein to enhance understanding of the present disclosure. A specific set of statements are provided as follows.

Statement 1: A method for treating leptomeningeal disease in a pediatric patient in need thereof, the method comprising administering to a patient a plurality of extraneous antineoplastons.

Statement 2: A method according to Statement 1, wherein the leptomeningeal disease is leptomeningeal, disseminated, and/or multicentric disease (LDM).

Statement 3: A method according to Statement 1, wherein the leptomeningeal disease is associated with one or more primary CNS tumors.

Statement 4: A method according to any one of the preceding Statements 1-3, wherein the leptomeningeal disease is associated with one or more low-grade gliomas (LGGs).

Statement 5: A method according to any one of the preceding Statements 1-4, wherein the plurality of extraneous antineoplastons comprises about a 4:1 ratio of synthetic phenylacetylglutaminate sodium (PG) and synthetic phenylacetylisoglutaminate sodium (iso-PG).

Statement 6: A method according to any one of the preceding Statements 1-5, comprising intravenous administration of the plurality of extraneous antineoplastons to the patient at a dosage of from about 0.5 g/kg/day to about 20 g/kg/day.

Statement 7: A method according to any one of the preceding Statements 1-4, wherein the plurality of extraneous antineoplastons comprises phenylacetylglutaminate sodium (PG) and phenylacetylisoglutaminate sodium (iso-PG), the method comprising intravenous administration of the plurality of extraneous antineoplastons in the following amounts: from about 0.4 g/kg/day to about 16 g/kg/day phenylacetylglutaminate sodium (PG); and from about 0.1 g/kg/day to about 4 g/kg/day phenylacetylisoglutaminate sodium (iso-PG).

Statement 8: A method according to any one of the preceding Statements 1-4, wherein plurality of extraneous antineoplastons comprises about a 4:1 ratio of phenylacetate (PN) and phenylacetylglutaminate (PG).

Statement 9: A method according to any one of the preceding Statements 1-4 and 8, comprising intravenous administration of the plurality of extraneous antineoplastons to the patient at a dosage of from about 0.08 g/kg/day to about 0.6 g/kg/day.

Statement 10: A method according to any one of the preceding Statements 1-4, and 8, wherein the plurality of extraneous antineoplastons comprises phenylacetate (PN) and phenylacetylglutaminate (PG), the method comprising intravenous administration of the plurality of extraneous antineoplastons in the following amounts: from about 0.064 g/kg/day to about 0.48 g/kg/day phenylacetate (PN); and from about 0.016 g/kg/day to about 0.12 g/kg/day phenylacetylglutaminate sodium (PG).

Statement 11: A method according to any one of the preceding Statements 1-4, wherein the plurality of extraneous antineoplastons comprises phenylacetylglutaminate sodium (PG), phenylacetylisoglutaminate sodium (iso-PG), and phenylacetate (PN).

Statement 12: A method according to any one of the preceding Statements 1-11, wherein the patient has undergone a tumor resection prior to the administration of the plurality of extraneous antineoplastons.

Statement 13: A method for treating leptomeningeal, disseminated, and/or multicentric disease (LDM) in a pediatric patient in need thereof, the method comprising administering to a patient a plurality of extraneous antineoplastons.

Statement 14: A method according to Statement 13, wherein the leptomeningeal disease is associated with one or more primary CNS tumors or one or more low-grade gliomas (LGGs).

Statement 15: A method according to Statement 13 or Statement 14, wherein the plurality of extraneous antineoplastons comprises phenylacetylglutaminate sodium (PG), phenylacetylisoglutaminate sodium (iso-PG), and phenylacetate (PN).

Statement 16: A method according to Statement 13 or Statement 14, wherein the plurality of extraneous antineoplastons comprises about a 4:1 ratio of synthetic phenylacetylglutaminate sodium (PG) and synthetic phenylacetylisoglutaminate sodium (iso-PG).

Statement 17: A method according to any one of the preceding Statements 13-16, comprising intravenous administration of the plurality of extraneous antineoplastons to the patient at a dosage of from about 0.5 g/kg/day to about 20 g/kg/day.

Statement 18: A method according to Statement 13 or Statement 14, wherein the plurality of extraneous antineoplastons comprises phenylacetylglutaminate sodium (PG) and phenylacetylisoglutaminate sodium (iso-PG), the method comprising intravenous administration of the plurality of extraneous antineoplastons in the following amounts: from about 0.4 g/kg/day to about 16 g/kg/day phenylacetylglutaminate sodium (PG); and from about 0.1 g/kg/day to about 4 g/kg/day phenylacetylisoglutaminate sodium (iso-PG).

Statement 19: A method according to Statement 13 or Statement 14, wherein the plurality of extraneous antineoplastons comprises about a 4:1 ratio of phenylacetate (PN) and phenylacetylglutaminate (PG).

Statement 20: A method according to Statement 13 or Statement 14, wherein the plurality of extraneous antineoplastons comprises phenylacetate (PN) and phenylacetylglutaminate (PG), the method comprising intravenous administration of the plurality of extraneous antineoplastons in the following amounts: from about 0.064 g/kg/day to about 0.48 g/kg/day phenylacetate (PN); and from about 0.016 g/kg/day to about 0.12 g/kg/day phenylacetylglutaminate sodium (PG).

Statement 21: A method according to any one of the preceding Statements 13-20, wherein the pediatric patient has undergone a tumor resection prior to the administration of the plurality of extraneous antineoplastons.

What is claimed is:

1. A method for treating leptomeningeal disease in a pediatric patient in need thereof, the method comprising intravenously administering to the pediatric patient a plurality of extraneous antineoplastons, wherein the plurality of extraneous antineoplastons comprises phenylacetylglutaminate sodium (PG), phenylacetylisoglutaminate sodium (iso-PG), and phenylacetate (PN), and wherein the leptomeningeal disease is not one or more gliomas (LGGs).

2. The method of claim 1, wherein the leptomeningeal disease is leptomeningeal, disseminated, and/or multicentric disease (LDM).

3. The method of claim 1, wherein the plurality of extraneous antineoplastons comprises about a 4:1 ratio of synthetic phenylacetylglutaminate sodium (PG) and synthetic phenylacetylisoglutaminate sodium (iso-PG).

4. The method of claim 2, comprising intravenous administration of the plurality of extraneous antineoplastons to the patient at a dosage of from about 0.5 g/kg/day to about 20 g/kg/day.

5. The method of claim 1, wherein the plurality of extraneous antineoplastons comprises phenylacetylglutaminate sodium (PG) and phenylacetylisoglutaminate sodium (iso-PG), the method comprising intravenous administration of the plurality of extraneous antineoplastons in the following amounts:
from about 0.4 g/kg/day to about 16 g/kg/day phenylacetylglutaminate sodium (PG); and
from about 0.1 g/kg/day to about 4 g/kg/day phenylacetylisoglutaminate sodium (iso-PG).

6. The method of claim 1, wherein the plurality of extraneous antineoplastons comprises about a 4:1 ratio of phenylacetate (PN) and phenylacetylglutaminate (PG).

7. The method of claim 3, comprising intravenous administration of the plurality of extraneous antineoplastons to the patient at a dosage of from about 0.08 g/kg/day to about 0.6 g/kg/day.

8. The method of claim 1, wherein the plurality of extraneous antineoplastons comprises phenylacetate (PN) and phenylacetylglutaminate (PG), the method comprising intravenous administration of the plurality of extraneous antineoplastons in the following amounts:
from about 0.064 g/kg/day to about 0.48 g/kg/day phenylacetate (PN); and
from about 0.016 g/kg/day to about 0.12 g/kg/day phenylacetylglutaminate sodium (PG).

9. The method of claim 1, wherein the plurality of extraneous antineoplastons comprises phenylacetylglutaminate sodium (PG), phenylacetylisoglutaminate sodium (iso-PG), and phenylacetate (PN).

10. The method of claim 1, wherein the patient has undergone a tumor resection prior to the administration of the plurality of extraneous antineoplastons.

11. A method for treating leptomeningeal, disseminated, and/or multicentric disease (LDM) in a pediatric patient in need thereof, the method comprising intravenously administering to the pediatric patient a plurality of extraneous antineoplastons, wherein the plurality of extraneous antineoplastons comprises phenylacetylglutaminate sodium (PG), phenylacetylisoglutaminate sodium (iso-PG), and phenylacetate (PN) and wherein the leptomeningeal, disseminated, and/or multicentric disease (LDM) is not one or more gliomas (LGGs).

12. The method of claim 11, wherein the plurality of extraneous antineoplastons comprises about a 4:1 ratio of synthetic phenylacetylglutaminate sodium (PG) and synthetic phenylacetylisoglutaminate sodium (iso-PG).

13. The method of claim 12, comprising intravenous administration of the plurality of extraneous antineoplastons to the patient at a dosage of from about 0.5 g/kg/day to about 20 g/kg/day.

14. The method of claim 11, wherein the plurality of extraneous antineoplastons comprises phenylacetylglutaminate sodium (PG) and phenylacetylisoglutaminate sodium (iso-PG), the method comprising intravenous administration of the plurality of extraneous antineoplastons in the following amounts:

from about 0.4 g/kg/day to about 16 g/kg/day phenylacetylglutaminate sodium (PG); and from about 0.1 g/kg/day to about 4 g/kg/day phenylacetylisoglutaminate sodium (iso-PG).

15. The method of claim 11, wherein the plurality of extraneous antineoplastons comprises about a 4:1 ratio of phenylacetate (PN) and phenylacetylglutaminate (PG).

16. The method of claim 11, wherein the plurality of extraneous antineoplastons comprises phenylacetate (PN) and phenylacetylglutaminate (PG), the method comprising intravenous administration of the plurality of extraneous antineoplastons in the following amounts:

from about 0.064 g/kg/day to about 0.48 g/kg/day phenylacetate (PN); and from about 0.016 g/kg/day to about 0.12 g/kg/day phenylacetylglutaminate sodium (PG).

* * * * *